(12) United States Patent
Orozco et al.

(10) Patent No.: US 9,529,035 B2
(45) Date of Patent: Dec. 27, 2016

(54) METHOD AND SYSTEM FOR LOCALIZATION OF OPEN DEFECTS IN ELECTRONIC DEVICES WITH A DC SQUID BASED RF MAGNETOMETER

(75) Inventors: Antonio Orozco, Washington, DC (US); Vladimir V. Talanov, Ellicott City, MD (US); Alfred Benjamin Cawthorne, III, Franklin, TN (US); Nicholas Eric Gagliolo, Washington, DC (US)

(73) Assignee: Neocera, LLC, Beltsville, MD (US)

( * ) Notice: Subject to any disclaimer, the term of this patent is extended or adjusted under 35 U.S.C. 154(b) by 221 days.

(21) Appl. No.: 14/351,396

(22) PCT Filed: Nov. 14, 2011

(86) PCT No.: PCT/US2011/060603
§ 371 (c)(1),
(2), (4) Date: Apr. 11, 2014

(87) PCT Pub. No.: WO2013/074068
PCT Pub. Date: May 23, 2013

(65) Prior Publication Data
US 2014/0253111 A1 Sep. 11, 2014

(51) Int. Cl.
*G01R 31/08* (2006.01)
*G01N 27/82* (2006.01)
(Continued)

(52) U.S. Cl.
CPC ............ *G01R 31/088* (2013.01); *G01N 27/82* (2013.01); *G01R 31/308* (2013.01);
(Continued)

(58) Field of Classification Search
CPC ............ G01R 33/0354; G01R 33/0356; G01R 33/0358
See application file for complete search history.

(56) References Cited

U.S. PATENT DOCUMENTS 3,544,889 A * 12/1970 Alauzet ............... G01R 5/28
324/455
5,004,724 A * 4/1991 De ...................... G01N 27/9033
257/32
(Continued)

FOREIGN PATENT DOCUMENTS

WO     WO 9418576 A2 *  8/1994   ......... G01R 33/0356
WO     WO 2008091712 A2 *  7/2008   ............. G01N 24/10

OTHER PUBLICATIONS

E.F. Fleet, et al., "High-Tc scanning squid microscopy of active circuits" in IEEE Transactions on Applied Superconductivity, 9(2):4103, 1999.
(Continued)

*Primary Examiner* — Huy Q Phan
*Assistant Examiner* — Adam Clarke
(74) *Attorney, Agent, or Firm* — Rosenberg, Klein & Lee

(57) ABSTRACT

Non-destructive localization of open defects in electronic devices is performed with a DC SQUID based RF magnetometer capable of sensing coherent magnetic fields up to 200 MHz and higher. RF magnetic fields (or RF current) images are correlated to conductive paths layout of the electronic device, and the open defect is pinpointed at a location of RF current disappearance on the current image. The bandwidth limitations associated with transmission line delays between SQUID circuit and readout electronic, as well as with near-field coupling between different parts of the measurement scheme, are overcome by superimposing the RF flux emanating from device under study on the modulation flux to produce at the SQUID output a binary phase modulated RF voltage, which is processed to lock the static flux, and to control modulation regime by producing an AC bias for the RF flux. RF readout electronics is based on a double lock-in through sequential demodulation of the
(Continued)

RF component of the output SQUID voltage at the modulation flux frequency $\omega_m$ and the RF flux frequency $\omega_{RF}$.

14 Claims, 12 Drawing Sheets

(51) Int. Cl.
  *G01R 33/035* (2006.01)
  *G01R 31/308* (2006.01)
  *G01R 31/315* (2006.01)

(52) U.S. Cl.
  CPC .......... *G01R 33/0356* (2013.01); *G01R 31/08* (2013.01); *G01R 31/315* (2013.01)

(56) References Cited

U.S. PATENT DOCUMENTS

| | | | | |
|---|---|---|---|---|
| 5,355,085 | A * | 10/1994 | Igarashi | G01R 33/0356 324/248 |
| 5,722,409 | A * | 3/1998 | Kuhara | G01R 33/56554 324/306 |
| 6,741,524 | B2 * | 5/2004 | Ichihara | G11B 5/00 360/59 |
| 7,106,057 | B2 * | 9/2006 | Matthews | B82Y 35/00 324/248 |
| 7,248,044 | B2 * | 7/2007 | Kobayashi | G01R 33/0354 324/248 |
| 8,593,141 | B1 * | 11/2013 | Radparvar | G01R 33/323 324/248 |
| 2006/0164081 | A1 * | 7/2006 | Ganther | G01R 33/0354 324/248 |
| 2011/0285393 | A1 * | 11/2011 | Zakosarenko | G01R 33/035 324/248 |

OTHER PUBLICATIONS

L. A. Knauss, et al., "Detecting power shorts from front and backside of IC packages using scanning squid microscopy" In Proc. of the 25th Int'l Symp. on Testing and Failure Analysis, p. 11, Santa Clara, CA, Nov. 1999.

J. P. Wikswo, "SQUID Sensors: Fundamentals, Fabrication and Applications" in chapter "The Magnetic Inverse Problem for NDE", pp. 629-695. Kluwer Academic Publishers, The Netherlands, 1996.

L.A. Knauss, et al., "Scanning squid microscopy for current imaging" in Microelectronics Reliability, 41: 1211-1229, 2001.

R. Dias, et al., "Integration of squid microscopy into FA flow In Proc. of the 27th Int'l Symp. on Testing and Failure Analysis," Santa Clara, CA, Nov. 2001.

D.P. Vallet, "Scanning squid microscopy for die level fault isolation" In Proc. of the 28th Int'l Symp. on Testing and Failure Analysis, pp. 391-396, Phoenix, AZ, Nov. 2002.

L. A. Knauss, et al., "Advances in scanning squid microscopy for die-level and package-level fault isolation" in Microelectronics Reliability, 43: 1657-1662, 2003.

D. Searls, et al., "Time domain reflectometry as a device packaging level failure analysis and failure localization tool" in Proc. of the 26th Int'l Symp. on Testing and Failure Analysis, pp. 285-291, Bellevue, WA, Nov. 2000.

D.A. Smolyansky, "Electronic package failure analysis using TDR" in Proc. of the 26th Int'l Symp. on Testing and Failure Analysis, pp. 277-283, Bellevue, WA, Nov. 2000.

T. K. Long, et al. "Time domain reflectometry technique for failure analysis" in Proc. of the 30th Int'l Symp. on Testing and Failure Analysis, pp. 61-622, Worcester, MA, Nov. 2004.

* cited by examiner

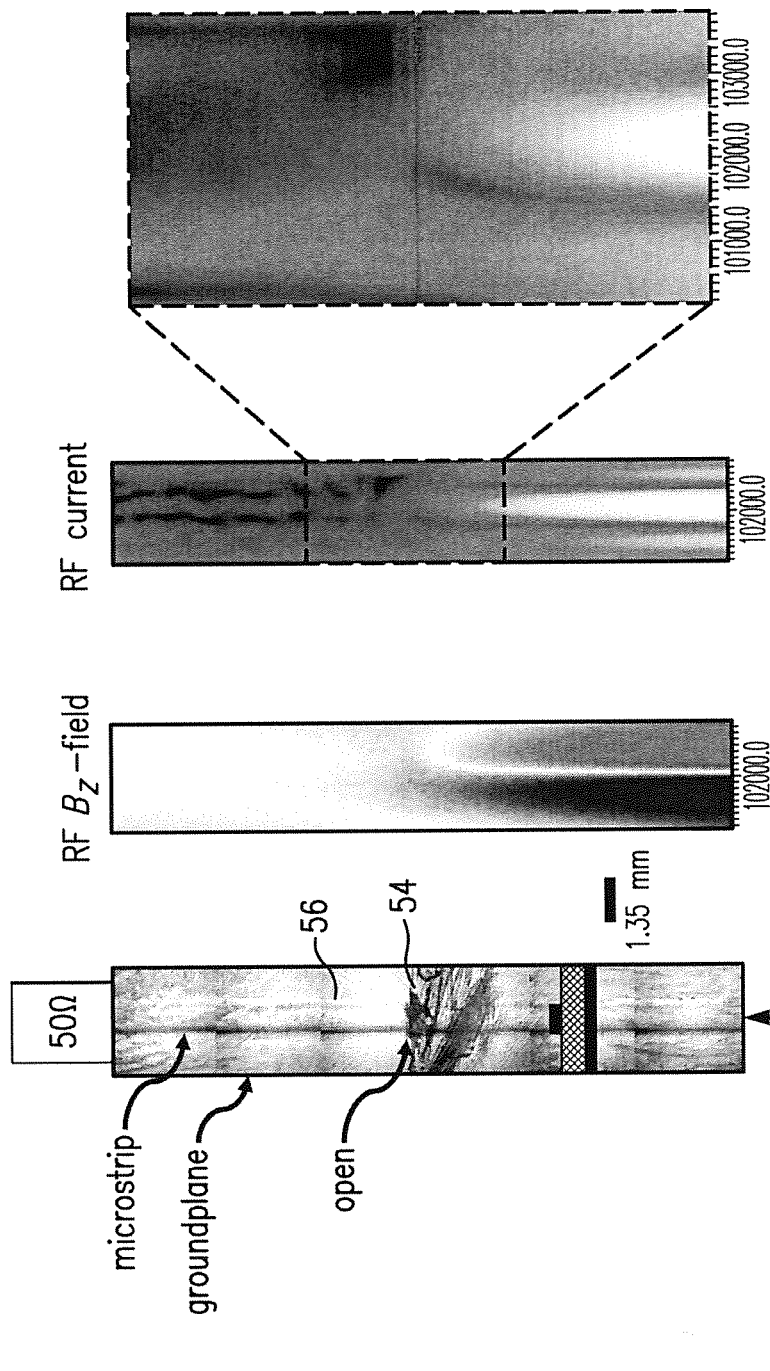

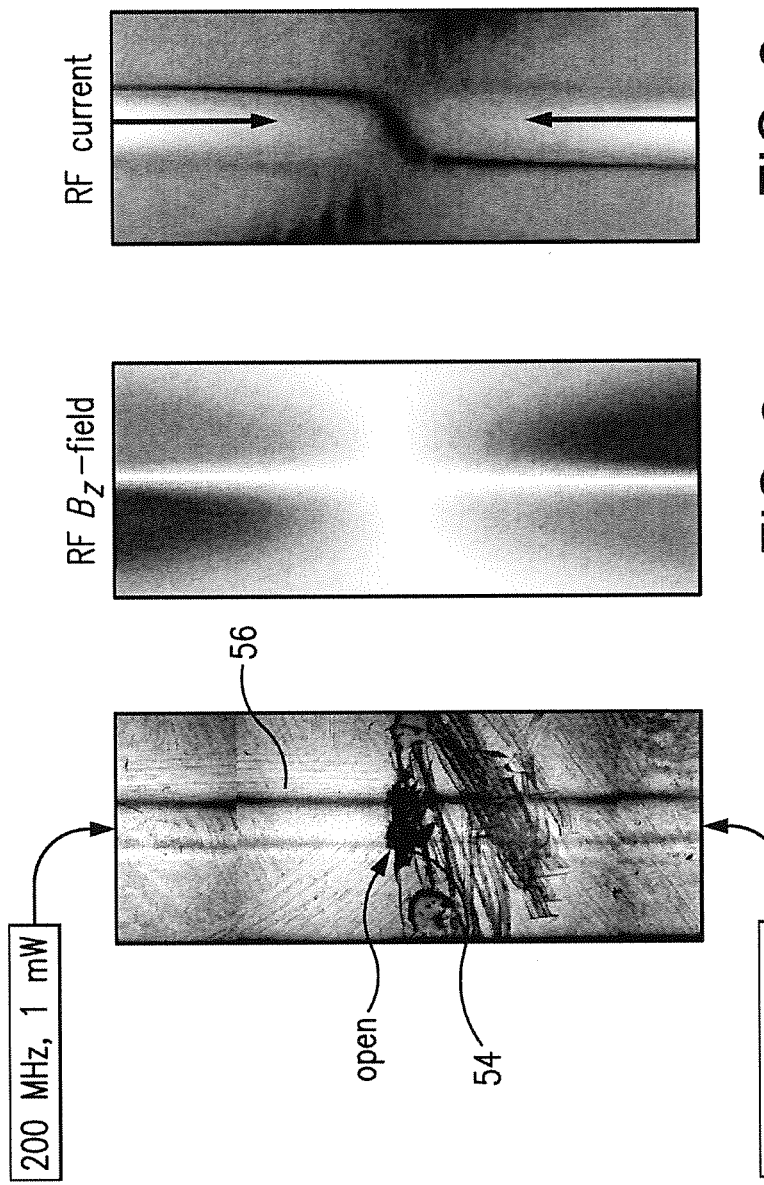

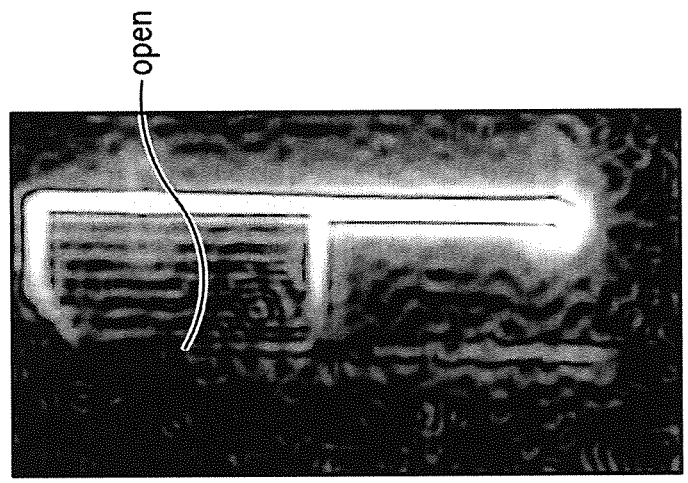
FIG. 12 Current
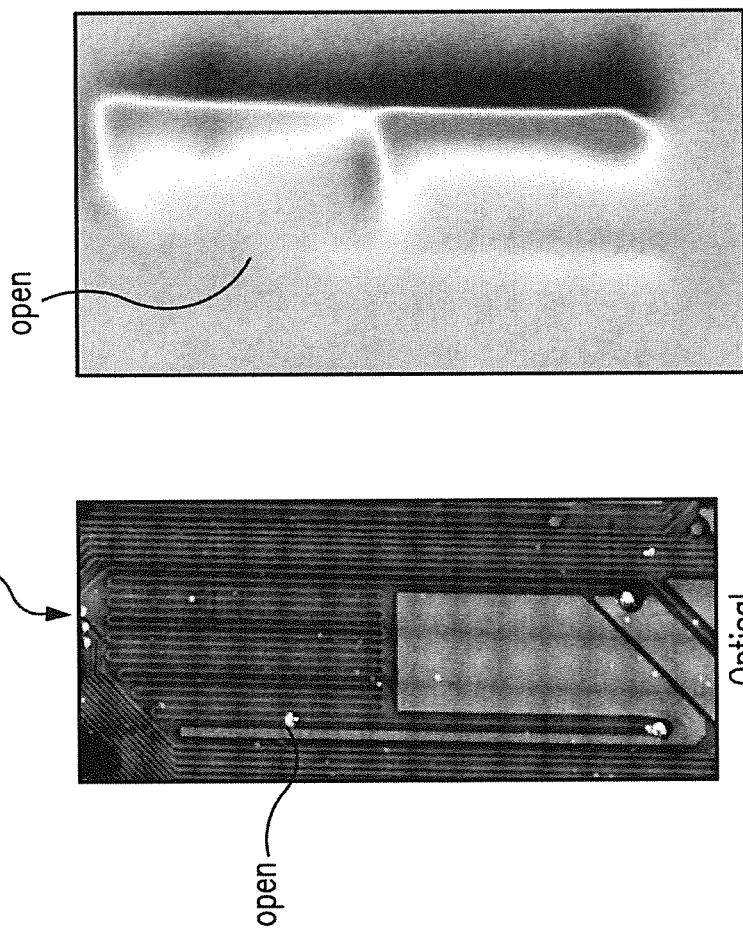
FIG. 11 $B_z$ @ 200 MHz
Image of dead open in IC
FIG. 10 Optical

METHOD AND SYSTEM FOR LOCALIZATION OF OPEN DEFECTS IN ELECTRONIC DEVICES WITH A DC SQUID BASED RF MAGNETOMETER

The work was funded by the NSF-SBIR contract Number IIP-0924610. The United States Government has certain rights to the Invention.

FIELD OF THE INVENTION

The present invention is directed to magnetic measurements for non-destructive isolation of defects in complex packages such as flip-chips, multi-chip modules and stacked dies which may include a number of metal layers and complex wiring paths. The invention specifically is related to magnetic currents imaging in electronic devices which is carried out with DC (direct current) Superconducting Quantum Interference Device (SQUID) based RF (radio frequency) magnetometer.

Further, the present invention is directed to a non-destructive detection of "dead" and resistive open defects by a DC SQUID based RF magnetometer capable of sensing coherent magnetic fields up to 200 MHz and higher.

In addition, the present invention is directed to a non-destructive localization of open defects in electronic devices through application of a DC SQUID based RF magnetometer operating in 200 MHz (and higher) bandwidth in which RF flux emanating from a device (sample) under study (integrated circuit, electronic package, etc.) is superimposed on the SQUID low-frequency modulation flux to produce a binary phase modulated RF voltage at the SQUID's output which is further demodulated with the use of a double lock-in technique (at the frequency $\omega_m$ of the modulation flux and at the frequency $\omega_{RF}$ of the RF flux) to produce an output signal which retains information about the amplitude and phase of the measured RF magnetic field.

In accordance with the overall underlying principle, the present invention is directed to a technique for non-destructive localization of an open defect in vicinity of a location where the detected RF magnetic fields (or RF magnetic currents) substantially disappear at the magnetic field (current) images acquired via application of a scanning DC SQUID based RF magnetometer.

BACKGROUND OF THE INVENTION

Magnetic current imaging is a technique for imaging buried currents in integrated circuits (ICs) and electronic packaged devices by detecting their magnetic fields (E. F. Fleet, et al., "High-$T_c$ scanning squid microscopy of active circuits" in *IEEE Transactions on Applied Superconductivity*, 9(2):4103, 1999; and L. A. Knauss, et al., "Detecting power shorts from front and backside of IC packages using scanning squid microscopy" In Proc. *Of the 25<sup>th</sup> Int'l Symp. On Testing and Failure Analysis*, page 11, Santa Clara, Calif., November 1999).

The detected magnetic fields are used to map currents in the device by using a Fourier Transform back-evolution technique (E. F. Fleet, et al., "High-$T_c$ scanning squid microscopy of active circuits," *IEEE Transactions on Applied Superconductivity*, 9(2):4103, 1999; and J. P. Wikswo, "*SQUID Sensors: Fundamentals, Fabrication and Applications*" in chapter "The Magnetic Inverse Problem for NDE", pages 629-695. Kluwer Academic Publishers, The Netherlands, 1996). The resulting current map is compared to a circuit diagram, an optical/infrared image or a non-failing part design to determine the fault location.

DC SQUIDs and low-frequency SQUID microscopy (L. A. Knauss, et al., "Scanning squid microscopy for current imaging" in *Microelectronics Reliability*, 41: 1211-1229, 1991; H. Weinstock, editor, "*SQUID Sensors: Fundamentals, Fabrication and Applications*" in Kluwer Academic Publishers, The Netherlands, 1996; and T. Van Duzer, et al., "*Principles of Superconductive Devices and Circuit*" in Prentice Hall, N.J., 2<sup>nd</sup> edition, 1999) are commonly used today for localizing shorts and high resistance defects and have become mainstream tools for package-level fault isolation (R. Dias, et al., "Integration of squid microscopy into FA flow" In *Proc. Of the 27<sup>th</sup> Int'l Symp. On Testing and Failure Analysis*," Santa Clara, Calif., November 2001) and effective tools for die-level fault isolation (D. P. Vallet, "Scanning squid microscopy for die level fault isolation" In *Proc. Of the 28<sup>th</sup> Int'l Symp. On Testing and Failure Analysis*, pages 391-396, Phoenix, Ariz., November 2002, and L. A. Knauss, et al., "Advances in scanning squid microscopy for die-level and package-level fault isolation" in *Microelectronics Reliability*, 43: 1657-1662, 2003).

DC SQUIDs and low-frequency SQUID microscopy have not been applied to open defects, however, since DC or low frequency signals cannot propagate along defective traces and thus do not produce currents in a circuit having an "open" defect.

Electrical opens are especially difficult to isolate since they do not conduct current. Unlike an open, a short may be isolated through thermal or current imaging techniques, and images with x-rays. However, open circuit failures which may be any of cracked metal traces, delaminated vias, C4 non-wet defects, Plated Through Hole (PTH) cracks, and any other package or interconnect structure defects, result in an electrically open signal line which renders the device unusable.

Currently, the main approach for localizing open circuit defects is Time Domain Reflectometry (TDR) (D. Searls, et al., "Time domain reflectometry as a device packaging level failure analysis and failure localization tool" in *Proc. Of the 16<sup>th</sup> Int'l Symp. On Testing and Failure Analysis*, pages 285-291, Bellevue, Wash., November 2000; D. A. Smolyansky, "Electronic package failure analysis using TDR" in *Proc. Of the 26<sup>th</sup> Int'l Symp. On Testing and Failure Analysis*, pages 277-283, Bellevue, Wash., November 2000; and T. K. Long, et al., "Time domain reflectometry technique for failure analysis" in *Proc. Of the 30<sup>th</sup> Int'l Symp. On Testing and Failure Analysis*, pages 61-622, Worcester, Mass., November 2004).

In TDR, a short electrical pulse is sent into a device under study, and the time to receive reflections is monitored. By comparing the reflected signal with that of non-defective parts, it is possible to localize a defect with a localization accuracy of up to 500 µm. In practice, 1-2 mm is the typical TDR localization accuracy, which is limited by the complex nature of wiring paths in a packaging under study.

Beyond the TDR, the only method for localizing the open defects is layer by layer deprocessing coupled with physical inspection under an optical microscope. The procedure may take weeks, and many times a defect may be missed through the optical inspection, or may actually be lost in the mechanical deprocessing.

In current failure analysis practice, shorts represent approximately 20% of the defects, high resistance shorts 10-15% of the defects, and opens are 60-70% of the defects encountered in packages. At a die level, shorts and opens appear with approximate equal probability.

Thus, there is strong interest from the semiconductor manufacturing industry in additional techniques for non-destructive localization of open circuit failures in electronic devices.

SUMMARY OF THE INVENTION

It is therefore an object of the present invention to provide a non-destructive technique for opens localization in electronic devices.

It is another object of the present invention to provide a technique for open defects localization which utilizes a high-sensitive DC SQUID based magnetometer, and particularly, a DC SQUID based RF magnetometer operable in bandwidth of up to 200 MHz and higher.

It is a further object of the present invention to provide an open localization technique where a DC SQUID based RF (or microwave frequency) magnetometer is utilized to acquire RF magnetic fields (or RF currents) images for an electronic device under study, and where the open defect is pinpointed at a location of the RF magnetic field (RF current) disappearance.

In addition, it is an object of the present invention to adapt a DC SQUID based magnetometer for operation in RF/microwave frequencies bandwidth (up to 200 MHz and higher) for application in open defects localization in electronic devices.

In one aspect, the present invention constitutes a method of detecting open defects. The detection of open defects is carried out through the steps of:

adapting a DC SQUID based magnetometer to operate at a Radio Frequency (RF) bandwidth up to 200 MHz and higher, scanning the tip of the DC SQUID over the electronic device under study, and acquiring images of magnetic field produced in conducting paths in the electronic device under study when RF powered.

The RF images of magnetic fields emanating from the electronic device under study may be first acquired as a function of relative disposition between the tip of the DC SQUID and the electronic device under study, and may be transformed into the current images through a Fast-Fourier Transform technique.

The procedure continues through overlaying the RF current images on an optical image of the wiring (conducting paths) layout of the electronic device, and pinpointing an open defect at a location on the wiring layout where the current image shows current disappearance.

The subject detection method is applicable at RF bandwidth ranging from 10 MHz to 200 MHz, and higher.

The RF power may be applied to the electronic device under study either in a single-ended, or differential feedline configuration.

In the differential feedline configuration, an amplitude imbalance between differential channels, as well as a phase difference between differential channels, may be introduced.

In order to adapt the DC SQUID circuit for operation at radio frequencies, bandwidth limitations due to delay in transmission lines connecting the SQUID circuit to room temperature electronics, as well as near field coupling, must be overcome. This is achieved in the subject system through the superposition of the RF flux $\Phi_{RF} \sin(\omega_{RF}t+\phi_{RF})$ emanating from the electronic device under study on a low-frequency modulation flux $\Phi_m \sin(\omega_m t+\phi_m)$ and inductively coupling both fluxes to the DC SQUID circuit, where $\Phi_m$, $\omega_m$ and $\phi_m$, are an amplitude, frequency, and phase of the modulation flux, respectively, and $\Phi_{RF}$ $\omega_{RF}$ and $\phi_{RF}$, are an amplitude, frequency and phase of the RF flux, respectively.

As a result, the DC SQUID circuit produces an output RF voltage binary phase modulated at a frequency $\omega_m$, between 0° and 180°. The SQUID's voltage is separated into an RF signal component and a low-frequency signal component. The RF signal component of the binary phase modulated output RF voltage produced by the SQUID circuit is demodulated sequentially by first and second demodulation units referenced to the $\omega_{RF}$ and $\omega_m$, respectively, to obtain at an output of the second demodulation unit, an output signal representative of the RF flux of interest.

The low-frequency signal component is fed into a flux-locked loop circuit to generate a feedback flux, and to lock the DC SQUID at quasi-static flux $n\Phi_0$, $n=0, 1, 2, \ldots$, where $\Phi_0$ is the magnetic flux quantum, in order to linearize the RF response (output RF voltage) of the SQUID circuit.

The second demodulation unit is coupled to the flux-locked loop circuit to control the low frequency modulation flux to the SQUID circuit.

In another aspect of the present invention, such constitutes a system for non-destructive detection of open defects in electronic devices through the use of a DC SQUID based RF magnetometer operating at a RF bandwidth (200 MHz and higher).

The subject system is designed with an X-Y-Z stage supporting an electronic device under study and controllably motioned by a computer unit which is operatively coupled to the stage and to the DC SQUID tip to controllably and selectively change relative disposition therebetween.

In the DC SQUID based RF magnetometer, a SQUID RF and AC electronics unit is coupled to the SQUID circuit to process the produced output RF SQUID voltage to generate an output signal ("IF signal") corresponding to measured magnetic fields emanating from the electronic device under study. At the same time, the SQUID RF and AC electronics unit is designed to control a flux locked loop regime of the SQUID operation and to overcome bandwidth limitations associated with transmission line delays between the SQUID circuit and readout electronics, as well as to near field "cross-talk" between various parts of the measurement system. The bandwidth limitations are overcome in the subject system by superimposing the RF flux emanating from the electronic device under study on the low frequency modulation flux to produce a binary phase modulated RF voltage at the SQUID circuit's output. This is processed in the SQUID RF and AC electronics unit.

Specifically, in the SQUID RF and AC electronics unit, a source of low-frequency modulation flux $\Phi_m \sin(\omega_m t+\phi_m)$ is inductively coupled to an input of the DC SQUID circuit, where $\Phi_m$ is the amplitude of the modulation flux, $\omega_m$ is the frequency of the modulation flux, and $\phi_m$ is the phase of the modulation flux, along with an RF flux $\Phi_{RF}(t)\sin(\omega_{RF}t+\phi_{RF})$ emanating from the electronic device under study and inductively coupled to the input of the DC SQUID circuit, where $\Phi_{RF}(t)$ is an amplitude of the RF flux, $\omega_{RF}$ is a frequency of the RF flux, and $\phi_{RF}$ is the phase of the RF flux.

Responsive to the RF flux and low-frequency modulation flux coupled thereto, the DC SQUID circuit produces an output RF voltage binary phase modulated at a frequency $\omega_m$ between 0° and 180°.

The SQUID RF and AC electronics unit includes a demultiplexing circuit coupled to the output of the DC SQUID circuit to separate the output RF voltage into an RF signal component and a low-frequency signal component, and an RF demodulation circuit receiving the RF signal component of the binary phase modulated output RF voltage. The RF demodulation circuit downconverts the RF signal component at the $\omega_m$ and $\omega_{RF}$ to produce an output signal representative of the RF flux emanating from the electronic device under study. The RF demodulation circuit includes a first demodulation unit referenced to the $\omega_{RF}$ and a second demodulation unit referenced to the $\omega_m$ and coupled to an output of the first demodulation unit.

The SQUID RF and AC electronics unit further includes a flux-locked loop (FLL) circuit coupled between the input and output of the DC SQUID circuit to inductively couple a feedback flux to the input of the DC SQUID circuit. The FLL circuit is coupled to an output of the demultiplexing circuit to receive the low-frequency signal component therefrom. The low-frequency signal component is processed in the FLL circuit to generate the feedback flux. The second demodulation unit is coupled to the FLL circuit to control the low-frequency modulation flux.

The first demodulation unit may include an RF lock-in amplifier referenced to $\omega_{RF}$, or an RF mixer/multiplier circuit. The second demodulation unit may include an Intermediate Frequency (IF) lock-in amplifier referenced to the $\omega_m$, or a multiplier circuit. The flux-locked loop (FLL) circuit may include an FLL lock-in amplifier referenced to the $\omega_m$, or a multiplier unit.

The source of low-frequency modulation flux may include a function generator producing the low-frequency modulation flux to be coupled to the flux-locked loop circuit and the second demodulation unit.

An RF power source is coupled to the electronic device via a single-ended or a differential feedline configuration. A modulation coil is located in close proximity to and inductively coupled to the DC SQUID circuit to couple the low-frequency modulation flux and the feedback flux to the DC SQUID circuit. An RF coil (either separate from or in a single configuration with the modulation coil) is located in close proximity of and inductively coupled to the DC SQUID circuit to couple the RF flux emanating from the RF flux to the DC SQUID circuit.

A data acquisition unit is operatively coupled to the SQUID RF and AC electronics unit to acquire images of magnetic fields or currents produced in conducting paths of the electronic device under study. The data acquisition unit operates under computer control.

Operatively coupled to the computer unit and the data acquisition unit, a data analysis unit functions to overlay the acquired current images onto an optical image of the conductive paths layout.

Further, an output unit is coupled to the data analysis unit to output a signal corresponding to an open defect location at an area of the conductive paths layout where the current image manifests current disappearance.

These and other features and advantages of the present invention will become apparent from the following detailed description of the present invention when taken in conjunction with the accompanying patent drawings.

BRIEF DESCRIPTION OF THE DRAWINGS

FIG. 3 is an image of an open defect in an RF microstrip with the RF power supplied to a single end of the microchip under study;

FIG. 4 is an RF magnetic field image corresponding to the microstrip image of FIG. 3;

FIG. 5 is an RF current image corresponding to the RF magnetic field image of FIG. 4;

FIG. 6 is the RF current image taken on an enlarged scale at the location of the detected open defect;

FIG. 7 is an image of an open defect in a microstrip line with RF power supplied to two ends of the microstrip in the in-phase sample excitation configuration;

FIG. 8 is the RF magnetic field image corresponding to FIG. 7;

FIG. 9 is the RF current image corresponding to the magnetic field image of FIG. 8;

FIG. 10 is a diagram of an IC package with an open defect;

FIG. 11 is a magnetic field image detected from the IC package shown in FIG. 10;

FIG. 12 is the RF current image corresponding to the magnetic field image of FIG. 11;

DETAILED DESCRIPTION OF THE PREFERRED EMBODIMENT

The present invention pursues the goal of employing DC SQUID based magnetometers to locate open defects in electronic devices.

It is known that DC and/or low-frequency (few KHz) periodic signals normally used in electrical probing, effectively carry no net current through a circuit defective trace in case of an open defect. The open defect may be in the form of cracked metal traces, delaminate vias, C4 non-wet defects, plated through hole cracks, and any other package or interconnect structure defect that results in an electrically open signal line which renders the device unusable.

Figure 1:
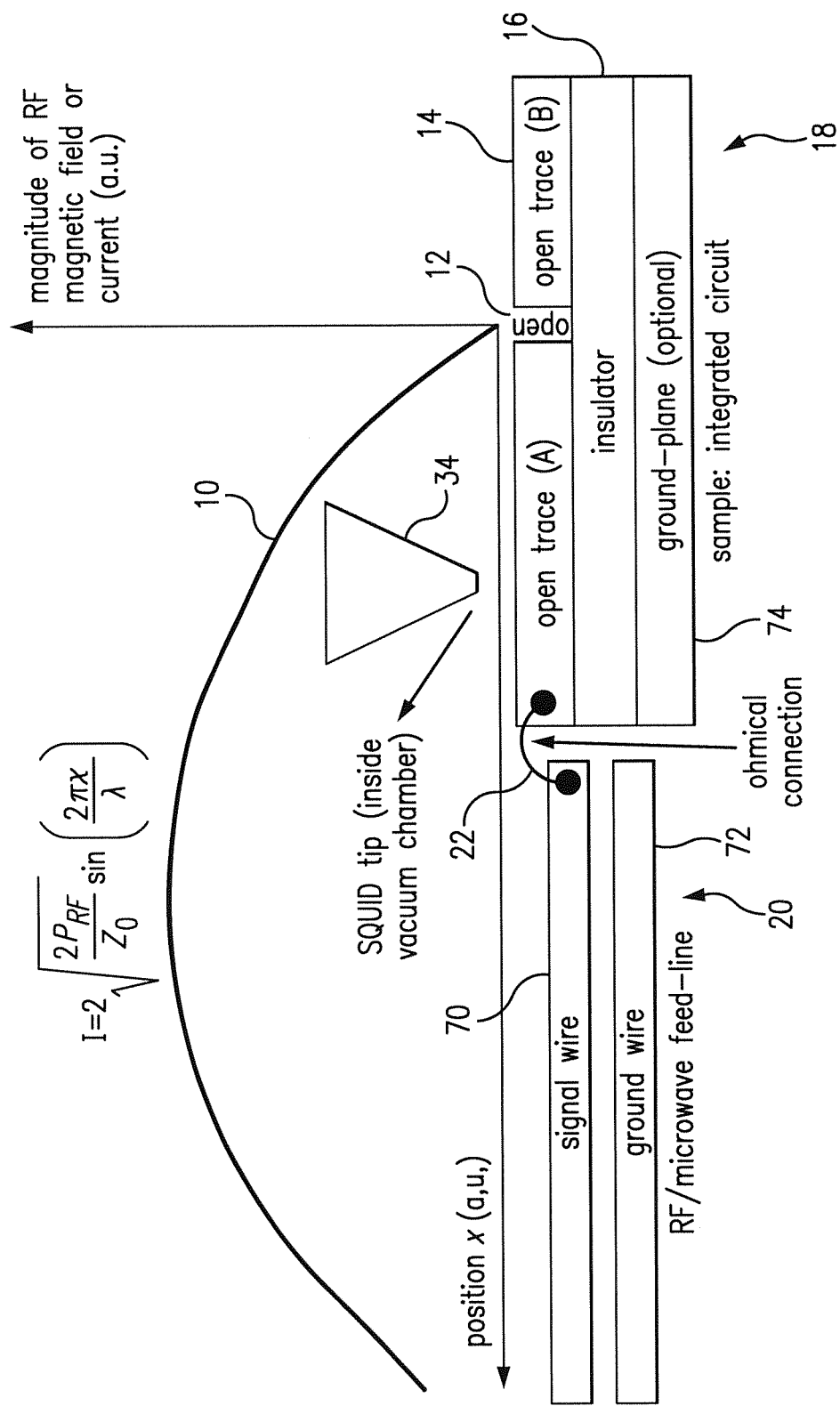
FIG. 1 is a schematic diagram representation of a snapshot of an RF standing wave formed in a defective conductive trace near an open.

However, when the frequency of the signal supplied to the circuit is brought into RF/microwave range, e.g. from 10 MHz to 100 GHz propagating along the conductive trace, the current/magnetic field node of such standing wave 10, shown in FIG. 1, coincides with the open 12 formed in the conductive trace 14 running on the top of the insulator layer 16 in the electronic device 18 under study. As shown in FIG. 1, which is a snapshot of the standing wave 10, the amplitude of the standing wave 10 is at a maximum and positive, assuming that characteristic impedances of the feedline 20 and the conductive trace 14 under study are matched.

Imaging the magnetic field produced by the standing wave 10 in the vicinity of the open 12 with a scanning DC SQUID based RF magnetometer permits recovery of the standing wave's profile and locate the open. As shown in FIG. 1, the magnetic field, as well as the current flowing in the conductive trace 14, is rather weak at the location of the open 12. However, the magnetic field, as well as the current, may be clearly imaged by scanning a SQUID based RF microscope over the electronic device 18 due to high sensitivity of the SQUID magnetometer.

An ohmical connection 22 is formed between the RF/microwave feed line 20 and the electronic device 18 under study. The feedline 20 may be in a single ended configuration or a differential configuration, as will be presented in further paragraphs. The RF/microwave feedline 20 serves for supplying RF or microwave power to the electronic device 18 under study to generate an RF current in the conductive paths.

Depending on the RF power, which may fall in a range of e.g. 0.001-10 mW, or lower, supplied to the electronic device, and the SQUID-device distance, which may fall in a range of e.g. 10-2000 microns, the sensitivity of the SQUID based RF magnetometer of the present invention is high enough to detect the magnetic field as close as few micron from the open (node). The RF current amplitude in the standing wave 10 near the open 12 may be estimated versus position X along the conductive trace 14 as:

$$I = 2\sqrt{\frac{2P_{RF}}{Z_0}} \sin\left(\frac{2\pi x}{\lambda}\right) \sim \sqrt{\frac{2P_{RF}}{Z_0}} \frac{2\pi x}{\lambda}$$ (Eq. 1)

where $P_{RF}$ is the RF power, $Z_0$ is the feedline characteristic impedance, and $\lambda$ is the radiation wavelength in transmission line formed by the trace. It is taken into account that for typical integrated circuits, at RF frequencies, $x \ll \lambda$.

Figure 2:
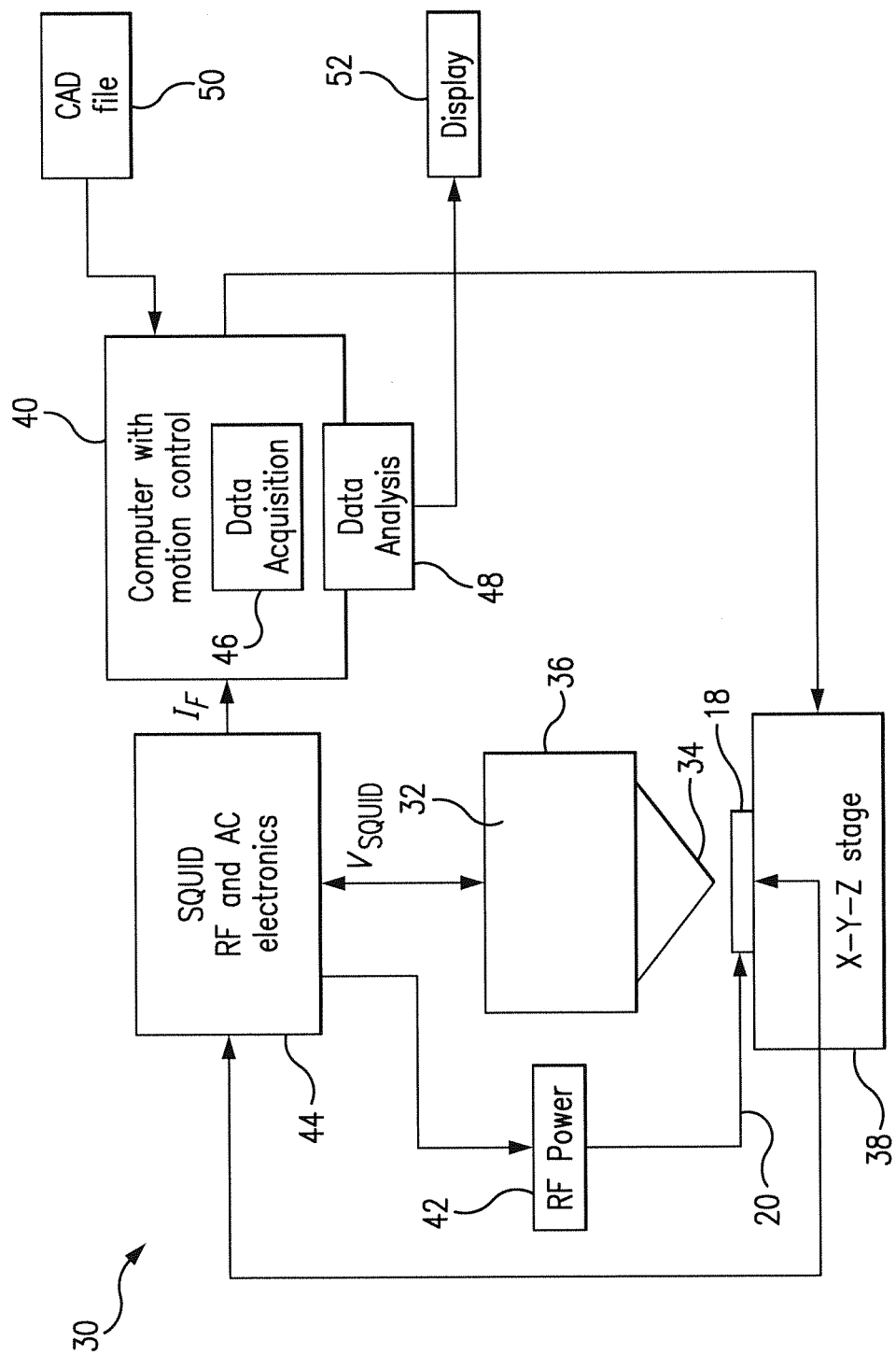
FIG. 2 is a simplified block diagram of the scanning DC SQUID based RF magnetometer system of the present invention for localization of open defects in electronic devices.

Referring to FIG. 2, the system 30 for locating open defects in an electronic device 18 includes a SQUID circuit 32 which is composed of two Josephson tunnel junctions that are connected together in a superconducting loop. Currents exist in the Josephson junction without any voltage drop up to a maximum value of the critical current $I_c$. When the SQUID is biased with a constant current $I_b$ that exceeds the critical current $I_c$ of the Josephson junction, the changes in the magnetic flux $\Phi$ threading the SQUID loop produces changes in the voltage drop across the SQUID.

SQUID magnetometer is the most sensitive detector of magnetic fields with the energy resolution approaching a quantum limit. The scanning SQUID magnetometer using a YBCO SQUID sensor is capable of measuring magnetic fields as small as 20 pt. The SQUID sensor is sensitive enough to detect a wire carrying a current as small as 10 nA at a distance of about 100 micrometer from the SQUID sensor.

The magnetometer allows the sample under investigation to be at room temperature and in air while the SQUID sensor must be under vacuum and cooled to less than 80 k using a cryocooler. During non-contact non-destructive imaging of a room temperature sample in air, the system may achieve a raw, unprocessed spatial resolution corresponding to the distance separating the SQUID tip 34 from the current.

As shown in FIGS. 1-2, the sensing part of the SQUID, i.e. SQUID tip 34 may be maintained inside a vacuum chamber a predetermined distance from the surface of the electronic device 18 under study. The SQUID circuit 32 is maintained in a vacuum chamber within a cryocooler 36.

The electronic device 18 under study is positioned on and supported by the X-Y-Z stage 38 which, under the control of computer system 40, can provide a 3-dimensional motion of the stage in order to change a relative disposition between the SQUID tip and the electronic device under study in horizontal as well as in vertical directions.

An RF/microwave power source 42 (which may be a part of the RF and AC electronics unit 44, as will be presented in following paragraphs) is coupled to the electronic device 18 under study in a single ended or differential configuration through the feedline 20.

When the electronic device 18 under study is powered by the RF (or microwave) energy, currents are produced in the conductive paths of the electronic device which results in magnetic fields emanating therefrom. The SQUID circuit 32, which is being scanned over the electronic device 18, acquires the magnetic field images of the fields emanating from the conductive paths.

The SQUID circuit 32, when sensing the magnetic fields, generates an RF voltage which is a periodic non-linear function of magnetic flux threading the SQUID loop $$V_{SQUID} = 0.5R\sqrt{I_b^2 - 4I_c^2 \cos^2(\pi\Phi/\Phi_0)}$$ (Eq. 2)

where R is the normal resistance of Josephson junction, $I_b$ is the SQUID bias current, $I_c$ is the Josephson critical current, $\Phi$ is the SQUID magnetic flux, and $\Phi_0 = \pi\hbar/e \sim 2.07 \times 10^{-15}$ Wb is the magnetic flux quantum with the reduced Planck constant $\hbar$ and the electron charge e.

The $V_{SQUID}$ is supplied to the SQUID RF and AC electronics unit 44 which will be presented in detail in conjunction with FIGS. 13-19. The SQUID RF and AC electronics unit 44 serves as means of operating the SQUID circuit in an optimal regime, to linearize the output SQUID voltage, and to produce an output signal IF representative of magnetic flux emanating from the electronic device free of noise (e.g. spurious signals) and in a linear format.

The magnetic field representative signal IF, in its turn, is supplied to a data acquisition unit 46 which collects the values of the magnetic fields along with scanning data to produce magnetic field images correlated to the X, Y and/or Z coordinates of the tip 34 position over the electronic device or along a conductive path.

The magnetic field images from the data acquisition unit 46 are transferred to a data analysis unit 48 which may use a Fast-Fourier Transform technique to transform the magnetic field images into the corresponding current images in the conductive paths of the integrated circuits or printed circuit boards under study. The resulting current map may then be compared (overlaid) to an optical image of a circuit diagram, for example, CAD files 50, in order to pinpoint a fault location.

The functions of the data acquisition unit 46 and the data analysis unit 48 are performed under the control of the computer system 40 and may be interchangeable in any desired fashion.

The current images may be presented in a form of current density images, as well as current peak images. The current density images give the magnitude of the current, while the current peak images reveal the current path with a ±3 µm resolution.

The system 30 outputs the image of magnetic field strength or current magnitude (after processing) versus position on the electronic device on a display unit 52 in some format, e.g., optical, electronic, digital, or printable, etc.

In the present system and method, the open defect location is detected at the location of the current disappearance. Referring to FIGS. 3-6, showing the detection of the open in an RF microstrip, the RF field of the frequency of 200 MHz and power of 1 mW may be supplied to a 50Ω microwave stripline where an open cut 54 is shown across the strip 56. The observed magnetic field shown in FIG. 4, is strong at the entry point and gradually disappears toward the location of the open 54. Inversion of the magnetic field into current shown in FIG. 5 and on the enlarged scale in FIG. 6, confirms that the current amplitude diminishes substantially to zero (noise level) at the open location. Since the map of the detected magnetic field, as well as the RF current, is aligned with the conductive paths layout, the location of the disappearance of the current may be correlated to the location of the open in the electronic device.

Referring to FIGS. 7-9, there are shown the principle of the detection of an open in 50 ohm microstrip line with RF power supplied to both ends of the microstrip line in-phase to produce RF currents at the opposite sides of the open to flow in opposite directions at any given time. FIG. 7 shows the imaging results of the RF power (200 MHz, 1 mW) supplied to the transmission line 56 with the open defect 54 crossing the transmission line 56. A diminished RF magnetic field at the location of the open is shown in FIG. 8. The location of the open may be clearly seen in FIG. 9 at the location of disappearance of the current.

Referring to FIGS. 10-12, presenting the detection of an open in an IC (Integrated Circuit) package, in order to study the ability of the scanning SQUID RF magnetometer to detect an open in a real IC package 60, a 10 micrometer wide laser cut open was created in IC package. The sample was powered up at a frequency of 200 MHz with power of 1 mW supplied at both ends of the IC using a 3 dB power splitter. The amplitude of the RF magnetic field shown in FIG. 11, which is strong at the entry points, and gradually decays toward the open location. Inversion of the magnetic field into current image, shown in FIG. 12, confirms that the current diminishes to zero (the noise level) at the open location. Despite the serpentine structure being a rather difficult structure to image (due to magnetic field cancellation by the neighboring traces), a location of the open with better than 11 micrometers spatial resolution has been attained.

Depending on the sample geometry and the open location, either a single-ended or a differential feedline configuration may be used to launch RF power into the open conductive trace. In the case of a single-ended feedline configuration, as shown in FIGS. 1 and 3, the feedline signal wire 70 is connected to the open trace 14 (or stripline 56 in FIG. 3). The ground wire 72, shown in FIG. 1, may be either left floating or may be connected to the sample ground plane 74. In the case of a differential connection, one of the wires, for example wire 76 which is a high (or low) wire, is connected to the open trace, and another wire 78, which is the low (or high) wire, is either left floating, or connected to the ground plane. The differential ground terminal is left floating.

It is also possible to launch the RF power into both sides of the open simultaneously as shown in FIG. 7, by splitting the RF power from a generator into two channels and connecting them to both sides of the open trace. Each channel may be connected either in single-ended or differential connection configuration as presented above. It is possible to introduce an amplitude imbalance between the two channels, as well as a phase difference, such as from 0 to 180 degree presented in FIG. 18 by using a 180° coupler 170.

The ultimate goal of the present invention is to employ a DC SQUID based RF magnetometer to detect an open defect in an electronic device 18 under study.

The use of a DC SQUID permits carrying out sensitive measurements of magnetic fields (or magnetic currents) in electronic devices. The ability of the DC SQUID based magnetometer to operate in RF (and even at microwave frequency) regions allows localization of "open" defects which is not possible for DC SQUID based magnetometers operating in DC or low-frequency diapasons, since DC or low frequency signals cannot propagate along a conductive path interrupted by an "open" defect.

An RF magnetometer based on the DC SQUID has been developed which is capable of detecting coherent magnetic fields at the bandwidth of 200 MHz and higher and which is applicable to open defects localization in electronic devices.

In the subject system 30, shown schematically in FIG. 2, the SQUID circuit 32 detects magnetic fields emanating from the electronic device 18 under study and generates a SQUID voltage presented in (Eq. 2).

The signal corresponding to $V_{SQUID}$ is supplied from the SQUID circuit 32 to the SQUID RF and AC electronic unit 44 presented in detail in FIGS. 13-18. The function of the unit 44 is to create an output IF signal, to be further discussed, that is a measure of RF magnetic field emanating from the electronic device of interest. The output IF signal is provided to the computer system 40, for obtaining a plurality of magnetic field values as the SQUID tip 34 is scanned over the electronic device 18. The data is supplied to the data analysis unit 48 for processing through FFT transformation and aligning the current images (shown in FIGS. 5, 9 and 12) with an optical image of device design layout 50. This pinpoints the open defect at the layout's location where the current image manifests disappearance of the current, i.e. where the value of the current diminishes practically to "0" (noise level). The RF current images overlaid with the optical image (CAD File) of the conductive paths layout is output to the display 52, in any output form (optical, digital, etc.) to show the location of the open defect.

Referring to FIGS. 13-18, the SQUID RF and AC electronics unit 44 of the system 30 utilizes a DC SQUID circuit 32 which is built with two Josephson tunnel junctions 90 connected together in a superconducting loop 92. When the SQUID circuit 32 is biased with a constant current that exceeds the critical current of the junction (the current existing in the junction without any voltage drop up to a maximum value of the critical current), the changes in the magnetic flux Φ threading the SQUID loop produce changes in the voltage drop across the SQUID, further referred to herein as SQUID response.

In order to linearize the SQUID response and increase its dynamic range, the SQUID magnetometer is operated in a flux-locked loop (FLL) regime. In this regime, a flux-locked loop circuit 94 is connected to the SQUID circuit 90 through a demultiplexing circuit 96.

The FLL circuit 94 includes a current source 98 (also referred to herein as "bias") producing the constant current $I_b$ to bias the SQUID circuit 32, decoupling capacitors 100, step up transformer 102, low noise amplifier 104, FLL lock-in amplifier 106, feedback resistors 108, current adder 110, and modulation coil 112 which is positioned in close proximity to the SQUID circuit 32 to inductively couple the modulation flux and the feedback flux to the SQUID circuit 32.

Figure 17:
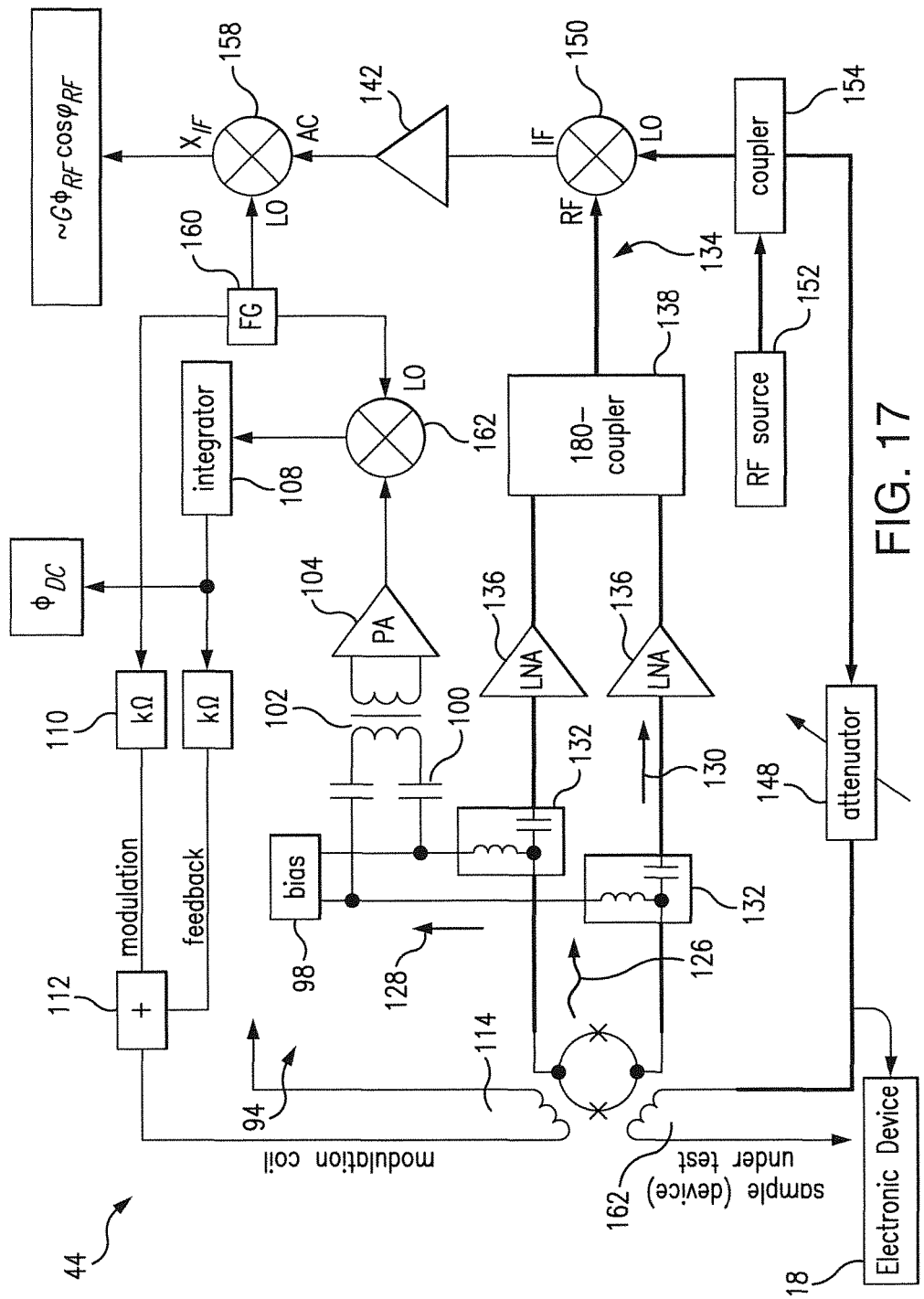
Figure 18:
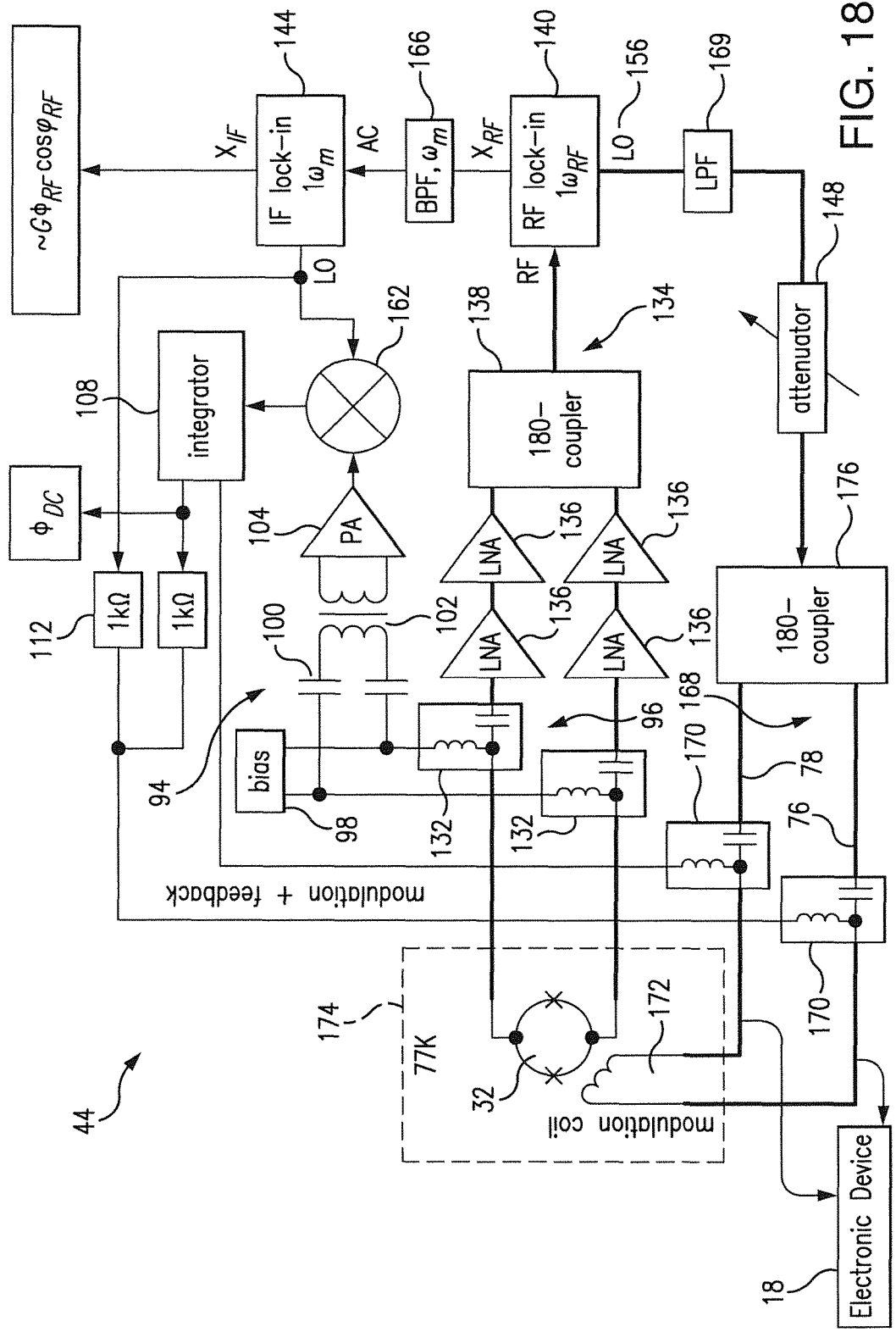
Figure 19:
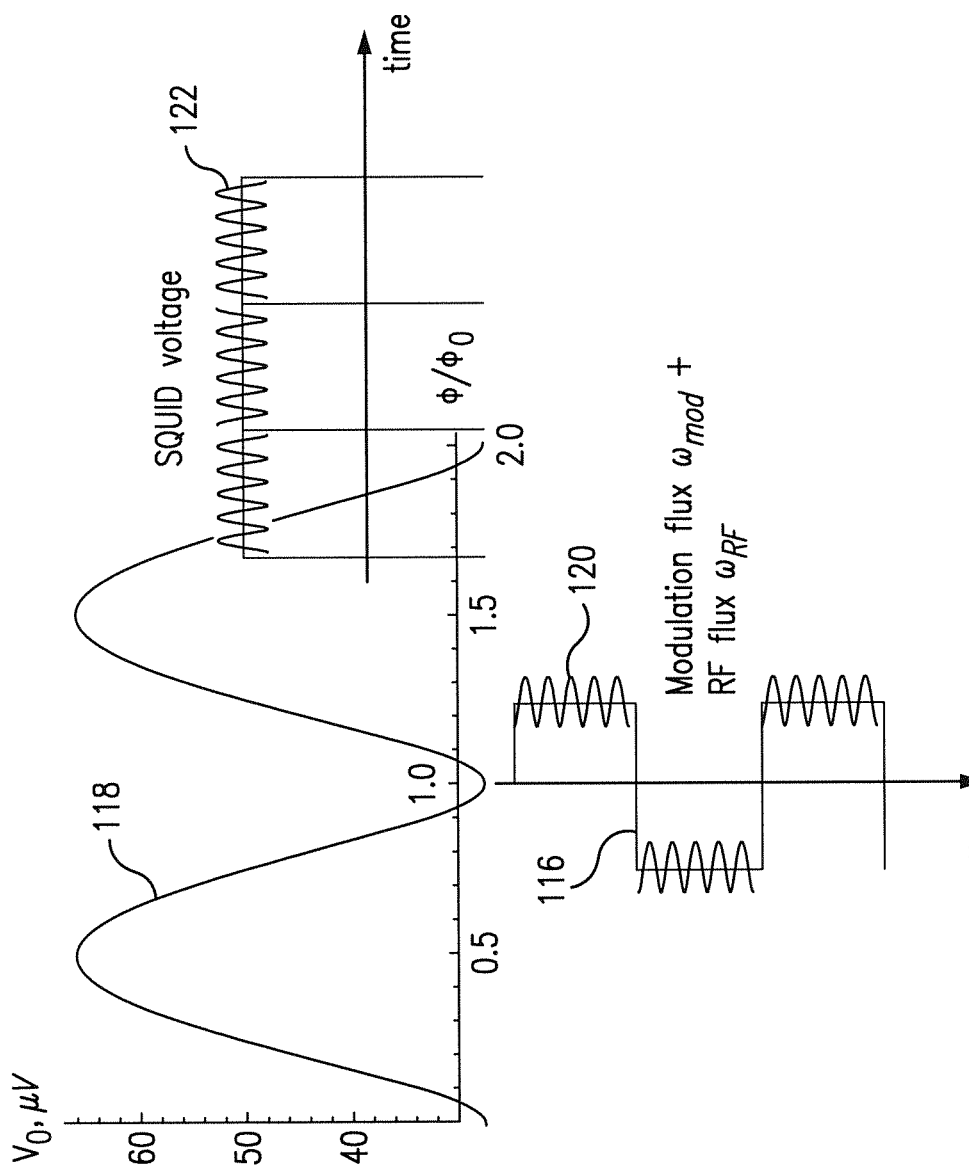
FIG. 19 is a V–Φ diagram illustrating principles of binary phase modulation for SQUID RF voltage with a square-wave modulation.

Referring to FIG. 19 and to FIGS. 13-18, a magnetic flux oscillating at the frequency of $\omega_m$ with an amplitude of about $\Phi_0/4$ is applied to the SQUID circuit 32 by means of the modulation coil 114 placed in close proximity and inductively coupled to the SQUID circuit 32. Modulation frequency $\omega_m$ may be in the range from 100 Hz to 10 MHz.

The lock-in amplifier 106 referenced to the frequency $\omega_m$ demodulates the SQUID output voltage whose output is integrated with the integrator 108, inverted, and fed back into the modulation coil through a feedback resistor 110 and the current adder 112.

When the SQUID's quasi-static flux is $n\Phi_0$, n=0, 1, 2, ..., the lock-in output of the FLL lock-in amplifier 106 is zero since the SQUID's voltage contains no fundamental harmonic. If the quasi-static flux is greater or lower than an $n\Phi_0$, the output of the lock-in amplifier 106 is positive or negative, respectively, with the feedback signal proportional to the quasi-static magnetic field $\Phi_{DC}$.

A modulation flux $\Phi_m \sin(\omega_m t+\phi_m)$ is applied to the SQUID circuit via modulation coil 114, and the SQUID quasi-static flux is "locked" at $n\Phi_0$. Considering the DC SQUID 32 incorporated into the FLL circuit 94 with the modulation flux $\Phi_m \sin(\omega_m t+\phi_m)$, which is "locked" to the minimum of V–$\Phi$ function $n\Phi_0$, the application of RF magnetic flux $\Phi_{RF}(t)\sin(\omega_{RF} t+\phi_{RF})$ to the SQUID makes the total flux threading the SQUID loop equal $$\Phi_{RF}(t)\sin(\omega_{RF}t+\phi_{RF})+n\Phi_0+\Phi_m \sin(\omega_m t+\phi_m) \qquad (Eq.\ 3)$$

If $\Phi_{RF}(t)<\Phi_0/4$ and $\Phi_m \sim \Phi_0/4$, the SQUID outputs an RF voltage which is binary phase modulated at $\omega_m$ between 0 degrees (for $\sin(\omega_m t+\phi_m)>0$) and 180 degrees (for $\sin(\omega_m t+\phi_m)<0$). For example, a square-wave modulation, shown in FIG. 19, would bias the SQUID at maximum slope of V–$\Phi$ function for each half-period. The square wave 116 is a low-frequency modulation flux used to provide an error (feedback) signal for FLL. During the first half-period modulation flux has a value of 1.25 $\Phi/\Phi_0$, and effectively biases the SQUID at the highest-positive slope of V–$\Phi$ curve 118. The same happens during the second half-period, when the modulation flux 116 is 0.75 $\Phi/\Phi_0$. However, the SQUID is biased at the highest-negative slope of V–$\Phi$ curve 118.

If an RF flux 120 is superimposed on top of the modulation flux 116, the SQUID will output RF voltage ("SQUID voltage") 122 with amplitude proportional to the slope of V–$\Phi$ curve at 1.25 $\Phi/\Phi_0$ or (0.75 $\Phi/\Phi_0$) multiplied by the amplitude of the RF flux 120. In other words, from an RF flux stand-point the SQUID appears to be "biased" at 1.25 $\Phi/\Phi_0$ and 0.75 $\Phi/\Phi_0$ during the first and second half-periods of modulation, respectively.

Further, the SQUID RF voltage 122 is binary phase modulated, between 0 and 180 degrees, at the modulation frequency $\omega_m$. RF voltage has the 0-degree phase (due to positive slope) during the first half-period of modulation, and has 180-degree phase (due to negative slope) during the second half-period of modulation.

Returning to FIGS. 13-18, after demultiplexing at the demultiplexing circuit 96, the SQUID voltage 126 is separated into a low frequency signal component 128 and RF frequency signal component 130. The demultiplexing circuit 96 may be implemented with a single bias-T circuit 132 (as presented in FIG. 14), or double bias-T circuits 132 (as shown in FIGS. 13 and 15-18) performing high-pass filtering for the SQUID's output RF voltage 126.

After isolation from the output SQUID's RF voltage 126, the RF signal 130 is processed by an RF demodulation circuit 134 in which the RF signal component 130 is first amplified with balanced low-noise RF amplifier(s) 136, and, as shown in embodiments presented in FIGS. 13 and 15-18, is converted from the differential into single-ended signal by a 180-degree coupler 138.

The coupler's output is demodulated by an RF lock-in amplifier 140 referenced to $\omega_{RF}$, which output, via an amplifier 142, is fed into intermediate frequency (IF) lock-in amplifier 144 referenced to $\omega_m$. For proper operation, the output bandwidth of the RF lock-in amplifier 140 is greater than $\omega_m$, i.e., $\omega_m$ falls within the output bandwidth of RF lock-in amplifier 140.

As presented in following paragraphs, the in-phase output $X_{IF}$ (IF signal) of IF lock-in amplifier 144 is proportional to both the amplitude and phase of RF magnetic field:

$$X_{IF}=G_{tot}\Phi_{RF}(t)\cos \phi_{RF} \qquad (Eq.\ 4)$$

where $G_{tot}$ is the total gain of the system.

Simultaneously, the DC output (low-frequency signal component 128) of the bias-T circuit 132 is fed into the FLL circuit 94 which feedback yields a traditional measure of the SQUID's static flux.

Due to the $\omega_{RF}>>\omega_m$, the RF and IF demodulation circuits 140 and 144, respectively, run simultaneously without affecting each other. The modulation flux output from the RF lock-in amplifier 140 serves both as an AC bias for the RF flux and as the modulation flux for the FLL circuit 94.

As shown in FIGS. 13-18, the demodulation circuit 144 (or 158) is coupled to the FLL 94 to determine the modulation regime. For example, in the case of a square-wave modulation (as shown in FIG. 19), the SQUID circuit 32 would be biased at the maximum slope (positive and negative) of V–$\Phi$ function for each half-period, respectively. Since the spurious RF signals originating outside the SQUID loop carry no phase modulation, they are efficiently eliminated by the double lock-in technique.

Figure 13:
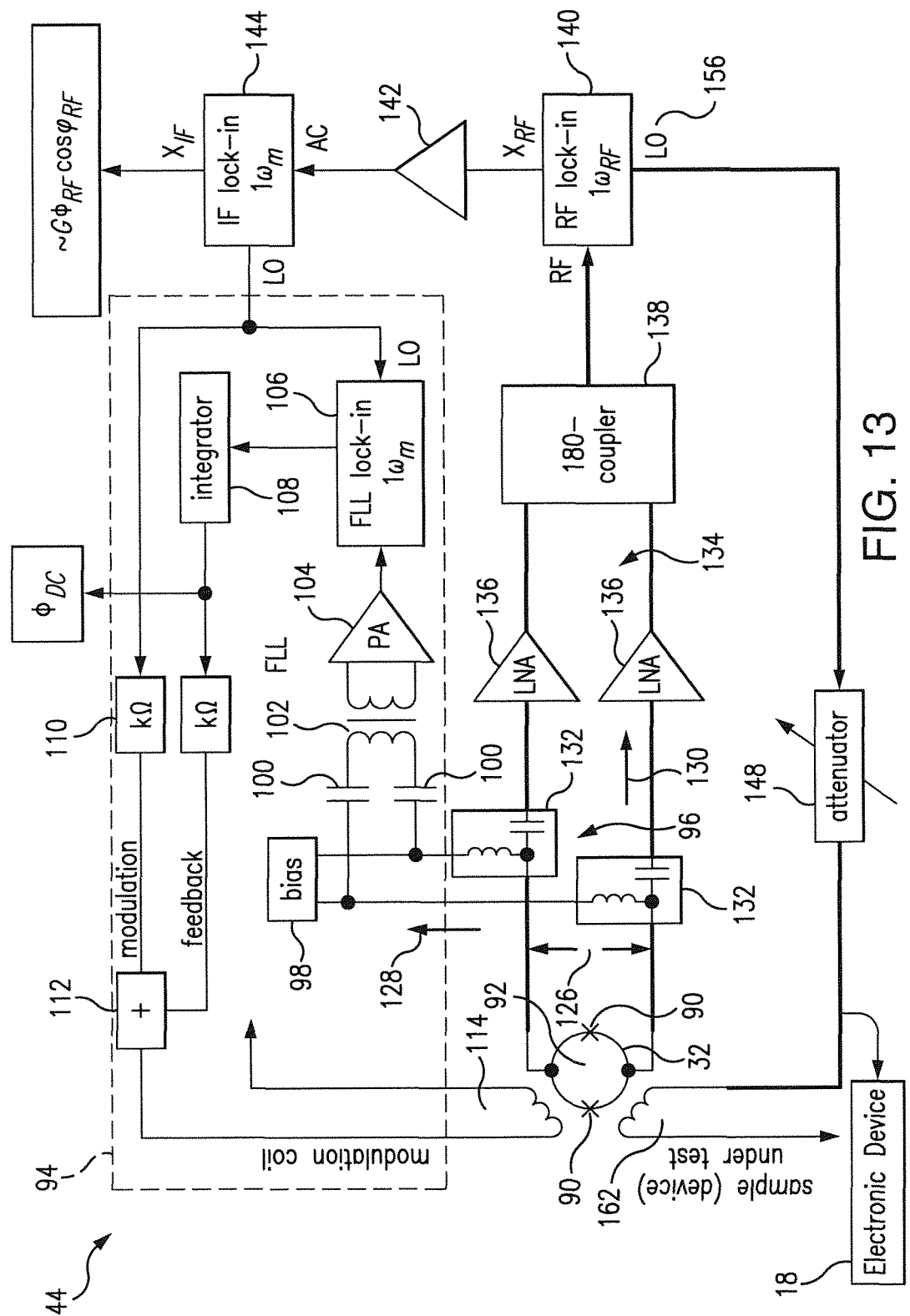
FIG. 13-18 are electrical block diagrams representative of alternative embodiments of the DC SQUID based RF magnetometer system of the present invention.
Figure 14:
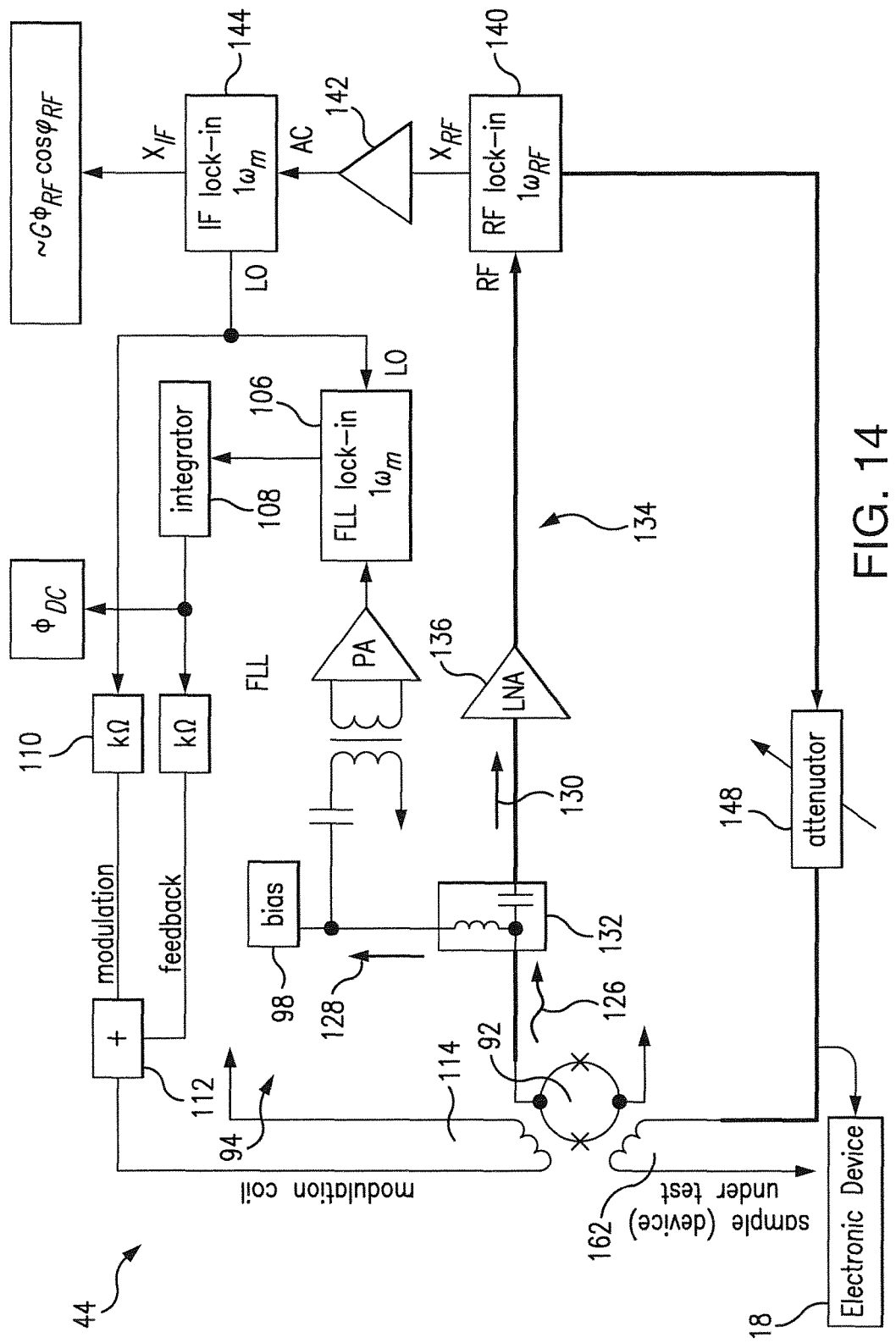

As shown in FIGS. 13-14, RF power is supplied from the RF lock-in 140 to the electronic device 18 via a variable attenuator 148. In this embodiment the range of RF frequency could be from 1 MHz up to 200 MHz.

In an alternative embodiment of the RF magnetometer of the present invention shown in FIG. 14, a single-ended configuration with a single bias-T circuit 132, single decoupling capacitor 100, and single RF LNA amplifier 136 is used in the RF demodulation circuit 134. In this embodiment, the 180-degree coupler 138 of FIG. 13 is omitted and the RF frequency bandwidth may range from approximately 1 MHz up to 200 MHz.

Figure 15:
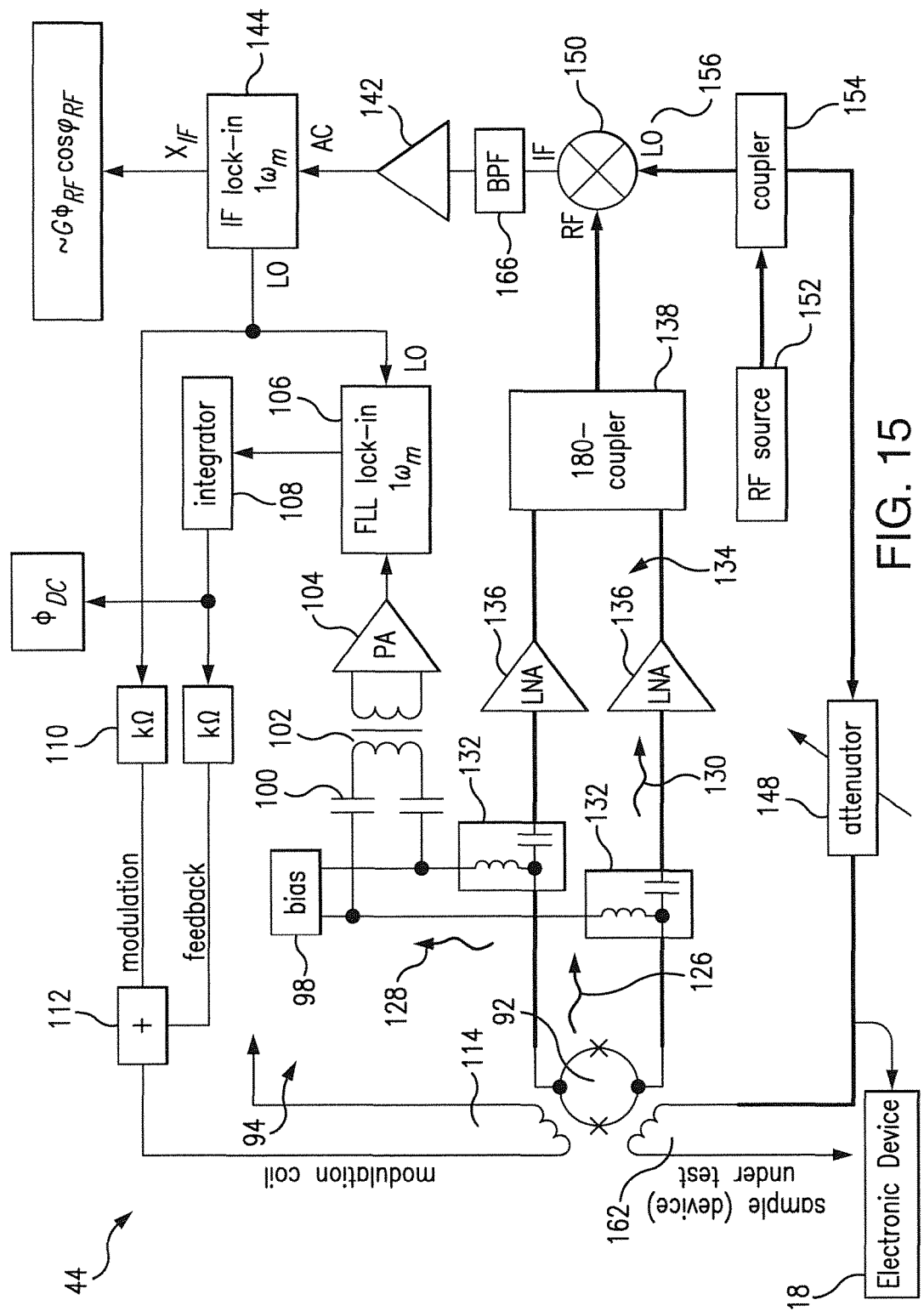
Figure 16:
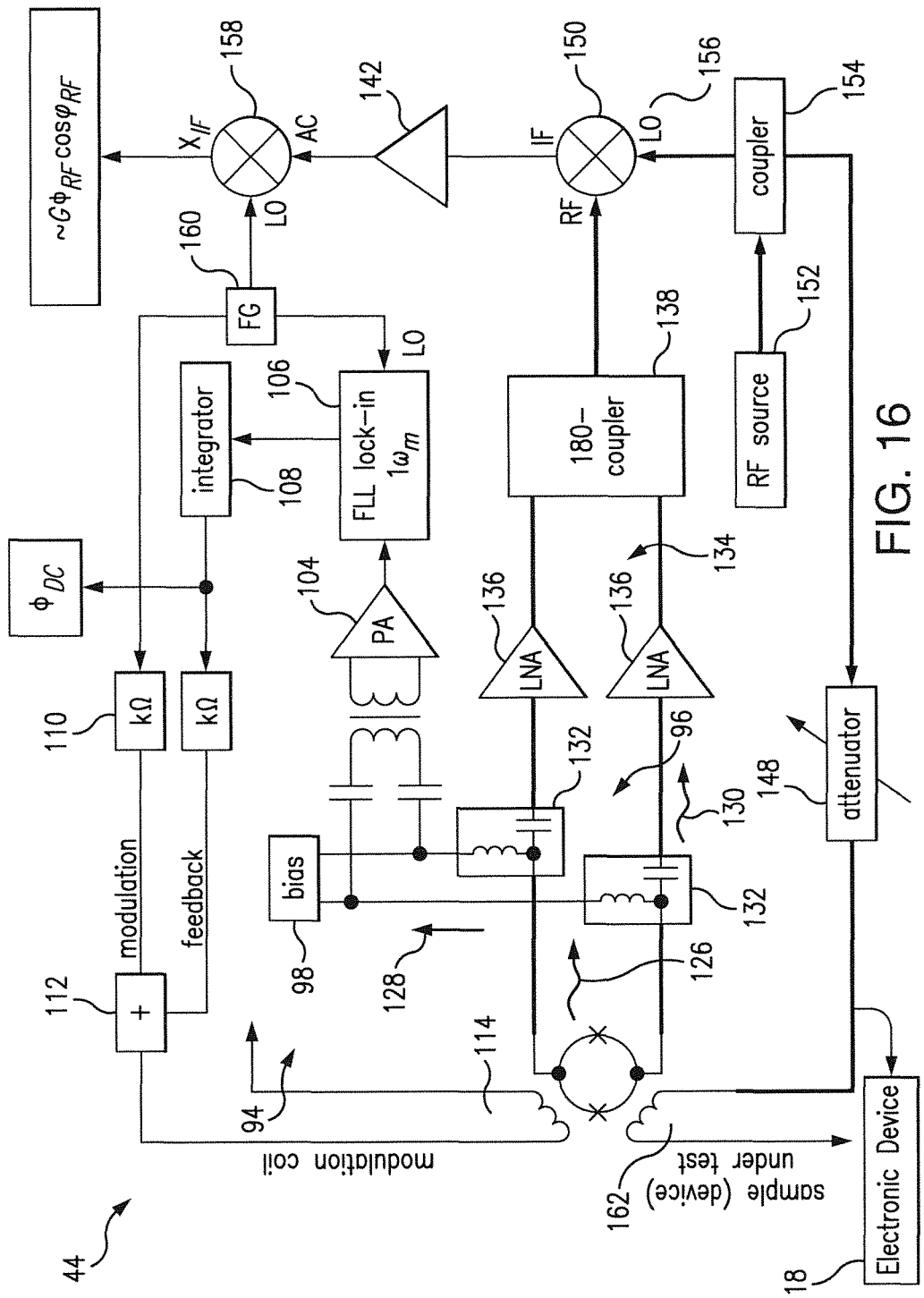

The RF lock-in amplifier 140, shown in FIGS. 13, 14 and 18, may be replaced by RF mixer/multiplier 150, as shown in FIGS. 15-17. In this case, the RF power from an RF source 152 is delivered via a coupler 154 to the mixer's 150 local-oscillator 156 and to the electronic device 18. In this embodiment the range of the RF frequency may extend from approximately 1 MHz up to 200 GHz.

As shown in FIGS. 15 and 18, a band-pass filter 166 may be coupled between the RF lock-in 14 (or mixer 150) and the amplifier 142.

Referring to FIG. 16, showing an additional version of the scheme presented in FIG. 15, IF lock-in amplifier 144 is replaced with a multiplexer 158. In this embodiment, a function generator 160 provides modulation signal to the FLL circuit 94 and the reference signal $\omega_m$ to the multiplier 158 through the local oscillator LO.

Referring to FIG. 17, which shows another embodiment of the scheme presented in FIG. 16, the FLL lock-in amplifier 106 is replaced with a multiplier 162.

Referring to FIG. 18, presenting a further alternative embodiment of the unit 44, the measuring scheme includes a differential line 168 through which the RF signal generated by the RF lock-in 140 is coupled to the SQUID circuit 32 enveloped in a cryogenic equipment 174. A low-pass RF filter 169 passes the filtered RF signal to the attenuator 148. The signal further is split in the 180-degree coupler 176 to become a differential signal which is fed into a pair of bias-T circuits 170 where the differential RF signal is combined with the modulation and feedback signals coming from the LLP 94. The superimposed signals are inductively coupled to the SQUID circuit 32 via the modulation coil 172. By varying the attenuator 148 settings, dependence of IF signal as a function of RF magnetic flux may be acquired.

Lock-In Simulation

To analytically model the double lock-in approach of the present invention, Eq. (1) can be approximated for $I_b>2I_c$ as follows:

$$V_{SQUID} = 0.25 RI_c \left( \frac{I_b}{I_c} + \sqrt{\frac{I_b^2}{I_c^2} - 4} + \left( \sqrt{\frac{I_b^2}{I_c^2} - 4} - \frac{I_b}{I_c} \right) \cos \frac{2\pi\Phi}{\Phi_0} \right) \quad \text{(Eq. 5)}$$

Around $\Phi = n\Phi_0$ ($n = 0, 1, 2, \ldots$), (Eq. 5) may be expanded as $$V(\Phi) = \frac{RI_c}{2} \sqrt{\frac{I_b^2}{I_c^2} - 4} + 2\pi^4 RI_c \left( \frac{I_b}{I_c} \sqrt{\frac{I_b^2}{I_c^2} - 4} \right) \left( \frac{\Phi}{\Phi_0} \right)^2 - \ldots \quad \text{(Eq. 6)}$$

Here $G_{SQUID} = [\partial V \cdot \partial \Phi]_{0.25\Phi_0} = \pi R I_c / \sqrt{2}$ (Eq. 7)

is the SQUID gain at $\Phi = (n+0.25)\Phi_0$.
The following fluxes are applied to the SQUID:
RF flux $\Phi_{RF} \sin(\omega_{RF}t + \phi_{RF})$,
modulation flux $\Phi_m \sin(\omega_m t + \phi_m)$, and
parasitic static offset from $n\Phi_0$ due to FLL imperfections $\Phi_{off}$.
The coherent spurious RF voltage at the input of RF lock-in 140 is $$V_{sp} \sin(\omega_{RF}t + \phi_{sp}) \quad \text{(Eq. 8)}$$

Taking into account a high-pass filtering effect of the bias-T 132, the total voltage seen by RF lock-in 140 is:

$$V_{RF} = G_{LNA} G_{SQUID} \Phi_{RF} \sin(\omega_{RF}t + \varphi_{RF}) \quad \text{(Eq. 9)}$$
$$(\Phi_{RF} \sin(\omega_{RF}t + \varphi_{RF}) + 2\Phi_m \sin(\omega_m t + \varphi_m) + 2\Phi_{off}) +$$
$$V_{sp} \sin(\omega_{RF}t + \varphi_{sp})$$

where $G_{LNA}$ is the LNA 136 voltage gain.
Multiplying (Eq. 6) by RF lock-in reference $G_{RF} \sin(\omega_{RF}t)$ and retaining only DC and low frequency terms yields for RF lock-in in-phase output:

$$X_{RF} = G_{RF} G_{LNA} G_{SQUID} \Phi_m \sin(\omega_m t + \phi_m) \Phi_{RF} \cos \phi_{RF} +$$
$$G_{RF} G_{LNA} G_{SQUID} \Phi_{off} \Phi_{RF} \cos \phi_{RF} + 0.5 G_{RF} V_{sp}$$
$$\cos \phi_{sp} \quad \text{(Eq. 10)}$$

where $G_{RF}$ is the total gain of RF lock-in.
Since signals associated with the parasitic DC offset and spurious RF voltage appear in Eq. 9 as DC terms, they are removed after IF lock-in demodulation 144. Multiplying (Eq. 9) by the IF lock-in reference $G_{IF} \sin(\omega_m t)$ yields IF lock-in in-phase output, that is IF signal:

$$X_{IF} = 0.5 G_{IF} G_{RF} G_{LNA} G_{SQUID} \Phi_m \cos \phi_m \Phi_{RF} \cos \phi_{RF} \quad \text{(Eq. 11)}$$

where $G_{IF}$ is the total gain of the IF lock-in 144.
By electing $\phi_m = 0$, the IF signal may be maximized:

$$X_{IF} = G_{TOT} \Phi_m \Phi_{RF} \cos \phi_{RF} \quad \text{(Eq. 12)}$$

where $G_{TOT} = 0.5 G_{IF} G_{RF} G_{LNA} G_{SQUID}$ is the net gain of entire system.
Both $G_{TOT}$ and $\Phi_m$ in the right hand side of (Eq. 11) are fixed and are well known.

Experimental Setup

A commercial $YBa_2Cu_3O_7$ DC SQUID on bi-crystal $SrTiO_3$ substrate with effective loop area of 32×32 μm² and single modulation coil was used for an open defect detection. The SQUID washer of 1×1 mm in size was glued onto the end face of tapered sapphire rod. The SQUID's critical current was 11 μA, normal junction resistance was 3 Ohm, contact resistance was less than 1 Ohm, and self-inductance was 200 pH. The measurements were done in a liquid nitrogen bath at 77.4 K without any shielding.

All electronics 44 were operated at room temperature and included three main sections (shown in FIGS. 13-18): synchronous RF demodulator 140 (or 150), synchronous IF demodulator 144 (or 158), and FLL 94.

Differential signaling, shown in FIG. 18, was implemented for low-level RF and AC signals, by wire-bonding the SQUID circuit 32 and modulation coil 172 terminals to the inner conductors of two pairs of 50Ω stainless steel coaxial cables. This approach takes advantage of both the SQUID and modulation coil being a naturally balanced source and load respectively, while eliminating a common mode noise, the differential connection 168, shown in FIG. 18. This also resolves the issue of impedance mismatch between the SQUID and RF electronics, which in turn leads to a wideband system.

RF demodulator includes two pairs of balanced ultra-low-noise amplifiers (LNAs) 136, 180-degree hybrid coupler 138, and RF lock-in amplifier 140 with 200 MHz RF bandwidth [SRS844]. After pre-amplification with the LNAs 136, the RF signal was converted from the differential into single-ended by 180-coupler 138 and was fed into RF lock-in 140 internally referenced to $\omega_{RF}$. Depending on the level of RF magnetic field, the net gain of RF lock-in 140 varied from $10^3$ to $10^5$. The best achievable RF lock-in sensitivity in the test setup was 100 μV ($10^5$ RF lock-in net gain), limited by the spurious RF signals. Since the RF lock-in had a minimal time constant of 100 μs, the maximum modulation frequency $\omega_m$ was limited at 2 kHz.

After passing through an active low-noise band-pass filter 166 centered at $\omega_m$, the output of RF lock-in was fed into IF lock-in 144 internally referenced to $\omega_m$. The IF lock-in net gain was 10, and the time constant was from 100 to 500 ms. A standing wave formed between the SQUID 32 and 180-coupler 132 created a spurious RF signal that was amplitude-modulated at 2 $\omega_m$. The spurious RF signal was rejected by the IF lock-in 144 referenced to $\omega_m$.

The double lock-in technique (RF lock-in and IF lock-in) utilized in the unit 144 of FIGS. 2-18 eliminates spurious RF signals due to coherent pick-up by the wiring loop connecting the SQUID to coaxial cables, near-field coupling (cross-talk) between the excitation and detection arms of entire setup, leakage of RF pick-up from DC into RF port of the bias-Ts, as well as RF leakage from LO (local oscillator) into RF port of the RF lock-in.

FLL 94 with 2 kHz sine-wave modulation and 100 Hz bandwidth was designed with capacitively coupled input transformer 102, differential ultra-low-noise preamplifier 104, FLL lock-in amplifier 106 externally referenced to $\omega_m$, integrator 108, and current adder 112. With 2 Ohm input resistor 110 at room temperature, the preamplifier 104 had a gain of $10^5$ and voltage noise density of <0.5 nV/√Hz at 2 kHz.

The DC SQUID based RF magnetometer capable of detecting coherent magnetic fields from 50 to 200 MHz and higher has been demonstrated for localization of open defects in electronic devices. The system offers the RF dynamic range of more than four orders of magnitude, with the flux noise density at 200 MHz of less than 4μ$\Phi_0$√Hz.

Unlike the existing SQUID FLLs with bandwidth restricted by transmission line delays in readout electronics, the upper frequency in the subject RF magnetometer is only limited by RF lock-in bandwidth and may be extended into GHz range by using a discreet multiplier (mixer), which also permits increasing the modulation frequency. An implementation of carrier/phase recovery module may aid in sensing the harmonic RF signals with unknown phase.

Although this invention has been described in connection with specific forms and embodiments thereof, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular locations of the elements may be reversed or interposed, all without departing from the spirit or scope of the invention as defined in the appended claims.

What is being claimed is:

1. A method for localizing open defects in electronic devices, comprising the steps of:
   (a) adapting a Direct Current (DC) Superconducting Quantum Interference Device (SQUID) based magnetometer to operate at a Radio Frequency (RF) bandwidth of 200 MHz and higher;
   (b) coupling an RF power to an electronic device under study;
   (c) scanning said DC SQUID based RF magnetometer over said electronic device under study with a distance between a tip of said DC SQUID and said electronic device under study ranging from 10 μm to 2000 μm;
   during the scanning, performing the steps of:
   (d) inductively coupling an RF flux $\Phi_{RF}$ sin $(\omega_{RF}t+\phi_{RF})$ emanating from said electronic device under study and superimposed on a low-frequency modulation flux $\Phi_m$ sin $(\omega_m t+\phi_m)$ to said DC SQUID,
   wherein $\Phi_m$, $\omega_m$ and $\phi_m$, are an amplitude, frequency, and phase of said modulation flux, respectively, and $\Phi_{RF}$, $\omega_{RF}$, and $\phi_{RF}$, are an amplitude, frequency and phase of said RF flux received from the electronic device under study, respectively, and wherein said $\omega_m \ll \omega_{RF}$, and said $\omega_m$ ranges from 100 Hz to below 10 MHz;
   (e) acquiring, at an output of said DC SQUID, an output RF voltage binary phase modulated at said frequency $\omega_m$ between 0° and 180°,
   (f) demultiplexing said output RF voltage into an RF signal component and a low-frequency signal component,
   (g) feeding said low-frequency signal component of said binary phase modulated output RF voltage into a flux-locked loop circuit coupled between an input and output of said DC SQUID to generate a feedback flux, and locking said DC SQUID at quasi-static flux $n\Phi_0$, n=0, 1, 2, . . . , where $\Phi_0$ is the magnetic flux quantum,
   (h) demodulating said RF signal component of said binary phase modulated output RF voltage at a first demodulation unit referenced to said $\omega_{RF}$ and a second demodulation units referenced to said $\omega_m$,
   (i) obtaining, at an output of said second demodulation unit, an output signal representative of said RF flux emanating from said electronic device under study, and
   (j) controlling said low-frequency modulation flux by coupling said second demodulation unit to said flux-locked loop circuit;
   (k) acquiring images of currents produced in a conducting path layout in said electronic device under study and correlated to said RF flux emanating from said electronic device under study;
   (l) aligning said current images with an image of said conducting path layout; and
   (m) pinpointing an open defect at a location of current disappearance on said current images correlated to said conducting path layout.

2. The method of claim 1, further comprising the steps of: prior to said step (k), performing the steps of:
   (n) acquiring RF images of the RF flux corresponding to magnetic fields emanating from said electronic device under study as a function of relative disposition between said tip of said DC SQUID based RF magnetometer and said electronic device under study, and
   (o) transforming said RF magnetic fields images into said currents images.

3. The method of claim 1, wherein said RF bandwidth ranges from 10 MHz to 200 MHz.

4. The method of claim 1, wherein said RF bandwidth is 200 MHz and higher.

5. The method of claim 1, wherein said RF power ranges from 0.001 mW to 10 W, or lower.

6. The method of claim 1, wherein said electronic device under study includes a microstrip transmission line.

7. The method of claim 1, wherein said electronic device under study is an Integrated Circuit (IC) package, and wherein in said step (b), said RF power is coupled to said IC at two ends thereof.

8. The method of claim 1, wherein in said Step (b), the RF power is coupled to said electronic device under study through a single-ended feedline configuration.

9. The method of claim 1, wherein in said step (b), the RF power is coupled to said electronic device under study through a differential feedline configuration.

10. The method of claim 9, further comprising the step of: creating an amplitude imbalance between differential channels in said differential feedline configuration.

11. The method of claim 9, further comprising the step of: creating a phase difference between differential channels in said differential feedline configuration.

12. A system for detecting open defects in electronic devices, comprising:
    a Direct Current (DC) Superconducting Quantum Interference Device (SQUID) based RF magnetometer operating at a radio frequency (RF) bandwidth, wherein said DC SQUID based RF magnetometer includes:
    a DC SQUID circuit,
    a source of low-frequency modulation flux $\Phi_m$ sin($\omega_m t+\phi_m$) inductively coupled to an input of said DC SQUID circuit, wherein $\Phi_m$ is the amplitude of the low-frequency modulation flux, $\omega_m$ is the frequency of the low-frequency modulation flux, and $\phi_m$ is the phase of the low-frequency modulation flux,
    said electronic device under study emanating an RF flux $\omega_{RF}(t)\sin(\omega_{RF}t+\phi_{RF})$ inductively coupled to said input of said DC SQUID circuit, wherein $\Phi_{RF}(t)$ is an amplitude of said RF flux, $\omega_{RF}$ is a frequency of the RF flux, and $\phi_{RF}$ is the phase of the RF flux, wherein said $\omega_m \ll \omega_{RF}$, and wherein said $\omega_m$ ranges from 100 Hz to below 10 MHz, and wherein, responsive to said RF flux and low-frequency modulation flux coupled thereto, said DC SQUID circuit produces an output RF voltage binary phase modulated at said frequency $\omega_m$ between 0° and 180°,
    a demultiplexing circuit coupled to an output of said DC SQUID circuit to separate said output RF voltage into an RF signal component and a low-frequency signal component,
    a flux-locked loop (FLL) circuit coupled between said input and output of said DC SQUID circuit to inductively couple a feedback flux $n\Phi_0$, n=0, 1, 2, ... to said input of said DC SQUID circuit, where $\Phi_0$ is the magnetic flux quantum, wherein said FLL circuit is coupled to an output of said demaultiplexing circuit to receive said low-frequency signal component therefrom, said low-frequency signal component being processed in said FLL circuit to generate said feedback flux $n\Phi_0$, an RF demodulation circuit receiving said RF signal component of said binary phase modulated output RF voltage and double-locking said RF signal component at said $\omega_m$ and $\omega_{RF}$ to produce an output signal representative of said RF flux emanating from said electronic device under study, said RF demodulation circuit including a first demodulation unit referenced to said $\omega_{RF}$ and a second demodulation unit referenced to said $\omega_m$, wherein said second demodulation unit is coupled to an output of said first demodulation unit and to said FLL circuit to control said low-frequency modulation flux;

a stage supporting said electronic device under study;

a computer unit operatively coupled to said stage and to a tip of said DC SQUID to controllably change relative disposition therebetween, wherein a distance between the tip of said DC SQUID and said electronic device under study ranges between 10 μm and 2000 μm:

a source of RF power coupled to said electronic device under study;

a data acquisition unit operatively coupled to said DC SQUID magnetometer to acquire images of currents produced in a conducting path layout of said electronic device under study;

a data analysis unit operatively coupled to said data acquisition unit, said data analysis unit correlating said current images with an image of said conducting path layout, said data acquisition unit and said data analysis unit being operatively coupled to said computer unit; and an output unit coupled with said data analysis unit and outputting a signal corresponding to an open defect location at an area of said conducting path layout where said current image manifests current disappearance.

13. The system of claim 12, wherein said first demodulation unit includes an RF lock-in amplifier referenced to $\omega_{RF}$, or an RF mixer/multiplier circuit;

wherein said second demodulation unit includes an Intermediate Frequency (IF) lock-in amplifier referenced to said $\omega_m$, or a multiplier circuit;

wherein said flux-locked loop (FLL) circuit includes an FLL lock-in amplifier referenced to said $\omega_m$, or a multiplier unit;

wherein said source of low-frequency modulation flux includes a function generator producing said low-frequency modulation flux to be coupled to said flux-locked loop circuit and to said second demodulation unit;

wherein said RF power source is coupled to said electronic device via a single-ended or a differential feedline; and wherein said system further includes a modulation coil located in close proximity of and inductively coupled to said DC SQUID circuit to couple said low-frequency modulation flux and said feedback flux to said DC SQUID circuit, and an RF coil located in close proximity of and inductively coupled to said DC SQUID circle to couple said RF flux emanating from said source of RF flux to said DC SQUID circuit.

14. The system of claim 12, wherein said $\omega_m$ falls within an output bandwidth of said first demodulator unit, and wherein said $\omega_{RF}$ is up to 200 MHz and higher.

* * * * *